US012576217B2

(12) United States Patent
McDonnell et al.

(10) Patent No.: US 12,576,217 B2
(45) Date of Patent: Mar. 17, 2026

(54) MULTI SURFACE ACOUSTIC NEBULISER

(71) Applicant: Royal Melbourne Institute of Technology, Melbourne (AU)

(72) Inventors: Amarin McDonnell, Ringwood North (AU); Amgad Rezk, Bayswater (AU); Leslie Yeo, Malvern East (AU)

(73) Assignee: Royal Melbourne Institute of Technology, Melbourne (AU)

( * ) Notice: Subject to any disclaimer, the term of this patent is extended or adjusted under 35 U.S.C. 154(b) by 1102 days.

(21) Appl. No.: 17/044,454

(22) PCT Filed: Apr. 5, 2019

(86) PCT No.: PCT/AU2019/050304
§ 371 (c)(1),
(2) Date: Oct. 1, 2020

(87) PCT Pub. No.: WO2019/191816
PCT Pub. Date: Oct. 10, 2019

(65) Prior Publication Data
US 2021/0100963 A1    Apr. 8, 2021

(30) Foreign Application Priority Data

Apr. 5, 2018    (AU) ................................ 2018901131

(51) Int. Cl.
*A61M 11/00* (2006.01)
*B05B 17/06* (2006.01)
(Continued)

(52) U.S. Cl.
CPC ......... *A61M 11/007* (2014.02); *A61M 11/005* (2013.01); *B05B 17/0676* (2013.01);
(Continued)

(58) Field of Classification Search
CPC ........ A61M 11/007; A61M 2205/0238; A61M 2205/0272; A61M 2205/0294;
(Continued)

(56) References Cited

U.S. PATENT DOCUMENTS 5,107,852 A * 4/1992 Davidson .............. A61M 25/09
604/528
5,299,739 A   4/1994 Takahashi et al.
(Continued)

FOREIGN PATENT DOCUMENTS

DE   102013019495 A1 * 5/2015 ......... A61M 11/001
EP       1602414 A2  12/2005
(Continued)

OTHER PUBLICATIONS

Conduit definition from MerriamWebster.com (Year: 2024).*
(Continued)

*Primary Examiner* — Tu A Vo
*Assistant Examiner* — Kelsey E Baller
(74) *Attorney, Agent, or Firm* — Westman, Champlin & Koehler, P.A.

(57) ABSTRACT

A nebuliser for nebulising liquid droplets includes a housing; at least one piezoelectric substrate accommodated within the housing and having a transducer surface upon which is located at least one electroacoustic transducer for generating acoustic wave energy within the substrate, and an opposing non-transducer surface; and a liquid supply system for supplying a liquid to at least one of the transducer and non-transducer surfaces. The liquid supply system includes a reservoir for accommodating the liquid, and at least one relatively rigid supply conduit in contact with the substrate for supplying the liquid from the reservoir to the substrate.

25 Claims, 8 Drawing Sheets

(51) Int. Cl.
  B06B 1/06     (2006.01)
  H10N 30/853    (2023.01)
(52) U.S. Cl.
  CPC .......... B06B 1/0611 (2013.01); B06B 1/0648
    (2013.01); H10N 30/8542 (2023.02); *A61M*
    *2205/0238* (2013.01); *A61M 2205/0272*
    (2013.01); *A61M 2205/0294* (2013.01); *B06B*
    *2201/20* (2013.01); *B06B 2201/55* (2013.01);
            *B06B 2201/77* (2013.01)
(58) Field of Classification Search
  CPC ........ A61M 2202/0468; A61M 11/005; A61M
    15/0085; A61M 2205/3334; A61M
    2205/3375; A61M 11/00–001; B05B
    17/0676; B05B 17/0607; B06B 1/0611;
    B06B 1/0648; B06B 2201/20; B06B
    2201/55; B06B 2201/77; B06B 1/06;
            H10N 30/8542
  See application file for complete search history.

(56)       References Cited

U.S. PATENT DOCUMENTS

| | | | |
|---|---|---|---|
| 6,161,536 A * | 12/2000 | Redmon .............. | A61K 9/0078 |
| | | | 128/200.14 |
| 6,679,436 B1 | 1/2004 | Onishi et al. | |
| 8,991,722 B2 | 3/2015 | Friend et al. | |
| 10,052,431 B2 * | 8/2018 | Dreschel .............. | B01D 21/283 |
| 2003/0175947 A1 * | 9/2003 | Liu ........................ | B82Y 30/00 |
| | | | 422/68.1 |
| 2014/0228736 A1 | 8/2014 | Eppstein et al. | |
| 2017/0178884 A1 * | 6/2017 | Murtazin ................ | G01J 3/443 |

FOREIGN PATENT DOCUMENTS

| | | | | |
|---|---|---|---|---|
| JP | 2008104966 A | | 5/2008 | |
| JP | 2013128569 A | * | 7/2013 | |
| WO | 2012096378 A1 | | 7/2012 | |
| WO | 2014132228 A1 | | 9/2014 | |
| WO | WO-2016179664 A1 | * | 11/2016 | ......... B05B 17/0615 |
| WO | 2018041106 A1 | | 3/2018 | |
| WO | 2019079857 A1 | | 5/2019 | |
| WO | 2019113639 A1 | | 6/2019 | |

OTHER PUBLICATIONS

Nib definition from Dictionary.com (Year: 2024).*
Conduit definition from dictionary.cambridge.org (Year: 2025).*
Friend et al., "Evaporative Self-Assembly Assisted Synthesis of Polymeric Nanoparticles by Surface Acoustic Wave Atomization", Nanotechnology, Mar. 4, 2008, 7 pages, vol. 19, No. 14.
Heron et al., "Surface Acoustic Wave Nebulization of Peptides as a Microfluidic Interface for Mass Spectrometry", Analytical Chemistry, 2010, pp. 3985-3989, vol. 82, No. 10.
Kurosawa et al., "Surface Acoustic Wave Atomizer", Sensors and Actuators A Physical, 1995, pp. 69-74, vol. 50.
Rajapaksa et al., "Effective Pulmonary Delivery of an Aerosolized Plasmid DNA Vaccine Via Surface Acoustic Wave Nebulization", Respiratory Research, May 20, 2014, 12 pages, vol. 15, No. 60.
Rezk et al., "HYbriD Resonant Acoustics (HYDRA)", Advanced Matter, Mar. 9, 2016, pp. 1970-1975, vol. 28, No. 10.
International Search Report and Written Opinion for International Patent Application No. PCT/AU2019/050304, dated Jun. 14, 2019.
Supplementary European Search Report in corresponding European Serial No. 19782244.8 dated Nov. 23, 2021.

* cited by examiner (d)

(e)

Atomisation without baffle

Atomisation with baffle

MULTI SURFACE ACOUSTIC NEBULISER

FIELD OF THE INVENTION

The present invention is generally directed to nebulisers for nebulising a liquid into small airborne droplets, and in particular to nebulisers using acoustic wave energy to nebulise the liquid.

BACKGROUND TO THE INVENTION

The use of surface acoustic waves (SAW) for the nebulisation of liquids has been proposed since the 1990's. See 'M. Kurosawa et al., 'Surface acoustic wave atomizer', Sensors and Actuators A: Physical, 1995, 50, 69-74'. SAW nebulisers have since found application in a variety of fields, including in the administration of active agents. Inhaled medication is the most common form of therapy for asthma, chronic obstructive pulmonary disease (COPD) and for other conditions associated with airflow limitation, such as obstructive bronchitis, emphysema, and cystic fibrosis. There has been extensive research and development in improving the performance of SAW nebulisation platforms in various applications including in fast drop ionization for interfacing with mass spectrometry (see 'S. R. Heron et al., 'Surface acoustic wave nebulisation of peptides as a microfluidic interface for mass spectrometry', Analytical Chemistry, 2010, 82, 3985-3989), nanoparticle synthesis (see 'J. R. Friend et al, 'Evaporative self-assembly assisted synthesis of polymeric nanoparticles by surface acoustic wave atomisation', Nanotechnology, 2008, 19, 1453010), and pulmonary delivery (see A. E. Rajapaksa et al., 'Effective pulmonary delivery of an aerosolized plasmid DNA vaccine via surface acoustic wave nebulization', Respiratory Research, 2014, 15, 1).

Despite these continued efforts, the current state-of-the-art has not progressed beyond the research laboratory environment to address issues associated with translating the platform for practical and commercial use. These issues, which are often overlooked by researchers, includes cumbersome and complex fluid chip to reservoir interfacing, weak flow rates, and spurious ejection of large droplets (often constituting a large proportion of the volume delivered), ultimately producing sub-optimal nebulisers that are custom-made to fit a particular laboratory application and can only be run by an expert user rather than a practical and commercially-realisable platform that can be used reliably and easily by end-users.

A particular challenge in using such SAW nebulisation platforms is with regard to issues surrounding the liquid used and their supply to the device. A common approach has been to supply the liquid using a wick placed on a transducer surface of a piezoelectric substrate. An electroacoustic transducer, typically in the form of interdigital transducers (IDTs), is photolithographically applied on the piezoelectric substrate so that the SAW can propagate on the transducer surface. An arrangement using a supply wick is for example shown in U.S. Pat. No. 8,991,722 (Monash University).

The use of a wick on the transducer surface can however lead to undesirable damping of the SAW, heating of the interfacial materials, and sensitivity of the performance depending on the spatial location of the liquid on the device, especially when the acoustic energy is focused on the chip. In addition, a trailing liquid film with a complex multi-step geometry is often present on the device during nebulisation, leading to the production of spurious large drops (>10 µm) and up to 100 µm in size, which are undesirable particularly for pulmonary drug delivery applications where droplets of the order of 1 µm are required for deep lung deposition.

One proposed arrangement to avoid at least some of the above noted issues is shown in International publication No 2014/132228 (RMIT University) where the supply wick is brought into contact with a peripheral edge of the piezoelectric substrate to thereby minimise the energy loss associated with the wick and supplied liquid being in contact with the transducer surface. Rather, the interaction of the SAW at the peripheral edge with the supplied liquid leads to the formation of a thin liquid layer from which atomisation can take place.

An alternative approach that has been proposed is to use conventional bulk acoustic waves (BAW) generated within the body of a piezoelectric substrate, rather than SAWs, to nebulise a liquid. U.S. Pat. No. 6,679,436 (Omron) describes a sprayer which uses conventional bulk waves for this purpose. While a SAW platform is used, the SAW is not used to nebulise but to sense the liquid (that is to sense if the liquid is present). Instead, the liquid is applied to the non-transducer surface of the piezoelectric substrate, and the bulk waves generated within the substrate are used to nebulise the liquid.

A problem associated with prior art SAW and BAW platforms is the relatively low nebulisation rates possible with such platforms. SAW platforms typically only have nebulisation rates of about 0.1 ml/min significantly limiting the potential applications of such platforms.

While it is a common belief that nebulisation platforms using SAW are the most efficient wave type, recent research has shown that a combination of both SAW and surface reflected bulk waves (SRBW) have been shown to provide superior liquid nebulisation. (see 'Amgad R. Rezk et al, 'Hybrid Resonant Acoustics (HYDRA)', Advanced Materials, 2016, 1970-1975'). The SRBW is generated when SAW on the transducer surface of the piezoelectric substrate internally reflects between the transducer surface and an opposing non-transducer surface of the substrate located in a parallel adjacent relationship to the substrate surface. The SRBW is therefore generated at the same frequency as the SAW. A hybrid acoustic wave combining both the SAW and SRBW is therefore generated due to their interrelationship, and manifests on both the transducer and non-transducer surfaces. The generation of the SRBW is optimised when the thickness of the substrate is at or around the wavelength of the generated SAW.

International Publication No. WO2016/179664 (RMIT University) describes a nebulisation platform using a hybrid acoustic wave combining SAW and SRBW for nebulising liquids. The liquid may be supplied to a side or end edge of the piezoelectric substrate using a wick or by dipping the substrate edge directly into a reservoir of the liquid. The hybrid acoustic wave (i.e., the SAW and SRBW) then acts to draw a thin film of liquid onto both the IDT surface and the non-IDT surface of the substrate. However, the combined SAW and SRBW nebulisation platform still faces similar concerns as those found in SAW only nebulisation platforms because of the use of a wick in contact with the substrate in one of the described embodiments.

These and other SAW nebuliser systems also suffer problems with performance reliability, reproducibility, efficiency and droplet distribution. In particular, systems utilising a single crystal chip are prone to failure due to overheating, pyroelectric failure, and, in some arrangements, require the chip to be in constant contact with a liquid sample. There is scope to improve the performance reliability and efficiency of such devices. Furthermore, achieving appropriate operating parameters, including but not limited to droplet size, geometric standard deviation (GSD) in droplet distribution, stabilization period (i.e. time to use), volumetric atomization rate, and fine particle fraction, for the administration of a diverse range of active pharmaceutical ingredients (APIs) remains a challenge.

The above discussion of background art is included to explain the context of the present invention. It is not to be taken as an admission that the background art was known or part of the common general knowledge at the priority date of any one of the claims of the specification.

The term, 'acoustic wave energy', will be used in the present specification to refer to both travelling and standing surface acoustic waves (SAW), and bulk acoustic waves (BAW) including surface reflected bulk waves (SRBW), and a combination of said waves, in particular, the combined SAW and SRBW.

The term, 'liquid', will be used in the present specification to refer to pure liquid, or liquid mixtures including functional or therapeutic agents such as pharmaceuticals, plasmid DNA, peptides, perfume and so on.

There is a need for an acoustic nebuliser that addresses one or more of the disadvantages associated with prior art acoustic nebulisers or at least provides an alternative.

SUMMARY OF THE INVENTION

With this in mind, according to one aspect of the present invention, there is provided a nebuliser including:
a housing;
at least one piezoelectric substrate accommodated within the housing and having a transducer surface upon which is located at least one electroacoustic transducer for generating acoustic wave energy within the substrate, and an opposing non-transducer surface; and
a liquid supply system for supplying a liquid to at least one of the transducer and non-transducer surfaces, the liquid supply system including a reservoir for accommodating the liquid, and at least one relatively rigid supply conduit in contact with the substrate for supplying the liquid from the reservoir to the substrate.

The supply conduit may be in the form of a nib or needle, and may be preferably formed from an acoustically reflecting material.

The liquid may be gravity fed from the reservoir through the supply conduit. The liquid may alternatively be transferred from the reservoir to the substrate through an active pumping system, for example, a syringe or peristaltic pump.

The liquid supply system may further include a flow regulator for providing a steady flow of liquid therefrom. The flow regulator may include a liquid outlet passage through which liquid can pass, and an air inlet passage connected to the reservoir.

An inner chamber may be connected to the flow regulator, the inner chamber having a peripheral opening within which is accommodated a peripheral tip of the supply conduit, wherein liquid can pass through capillary action between the peripheral opening and peripheral tip of the supply conduit.

The substrate may be supported on a displaceable mount for controlling the contact of the substrate with the supply conduit. The mount may, for example, include a pivot support at one end thereof, and an opposing end supported on a resilient member. Alternatively, the mount may be supported on a cantilever.

According to another aspect of the present invention, there is provided a nebuliser for nebulising liquid droplets, including:

a housing;
at least one piezoelectric substrate accommodated within the housing and having a transducer surface upon which is located at least one electroacoustic transducer for generating acoustic wave energy within the substrate, and an opposing non-transducer surface
a compliant material in contact with at least a portion of the perimeter surface of the at least one piezoelectric substrate; and
a liquid supply system for supplying a liquid to at least one of the transducer and non-transducer surfaces, the liquid supply system including a reservoir for accommodating the liquid, and at least one supply conduit for supplying the liquid from the reservoir to the substrate.

The compliant material may include self-adhesive tape, silicone rubber, thermal paste, and combinations thereof.

The nebuliser may further include a control means for controlling the size of the nebulised liquid droplets. The control means may include at least one baffle located in a generally parallel and adjacent relationship to at least one of the transducer surfaces. The substrate may be supported within a housing, and the baffle(s) included as the droplet size control means may be provided by a housing inner wall located in a parallel adjacent relationship from at least one said substrate surface. In another embodiment, the control means for controlling the size of the nebulised liquid droplets may alternatively be provided by active substrate baffling.

The housing may further include an inlet opening, and the reservoir may include a neck portion that can be accommodated within the inlet opening. This can allow the liquid held within the reservoir to be gravity fed to the at least one substrate.

The nebuliser according to the present invention may include at least two said substrates spaced apart and located in a parallel adjacent relationship. The droplet size control means may further include pre-setting the spacing between the substrates to control the thickness of the meniscus of the liquid supplied between the adjacent substrate surfaces, to thereby control the size of the nebulised droplets. Alternatively, the droplet size control means may further include pre-setting the spacing of the substrates from the internal walls of the housing to control the thickness of the meniscus of the liquid supplied between the adjacent substrate surface and inner wall, to thereby control the size of the nebulised droplets.

The generated acoustic wave energy may include surface acoustic waves (SAW) propagated in the transducer surface of the at least one substrate. The acoustic wave energy may include surface reflected bulk waves (SRBW) reflected between the transducer and non-transducer surfaces of the at least one substrate. In an embodiment, the acoustic wave energy may include a combination of surface acoustic waves (SAW) and surface reflected bulk waves (SRBW). The surface acoustic waves (SAW) may include standing waves, traveling waves and combinations thereof. The surface reflected bulk waves (SRBW) may include standing waves, traveling waves and combinations thereof. As previously noted, SRBW is generated when SAW on the transducer surface of the piezoelectric substrate internally reflects between the transducer surface and an opposing non-transducer surface of the substrate located in a parallel adjacent relationship to the substrate surface (i.e. the other side of the substrate). The SRBW is therefore generated at the same frequency as the SAW. A hybrid acoustic wave combining both SAW and SRBW may be generated due to their interrelationship, and manifests on both the transducer and opposing non-transducer surfaces.

As noted above, a liquid supply system may supply a liquid to at least one of the transducer and the non-transducer surfaces. In view of this and the fact that acoustic waves may be manifested on both the transducer and opposing non-transducer surfaces, it is appreciated that a liquid sample may be nebulised from the transducer surface, the opposing non-transducer surface, or both the transducer and opposing non-transducer surfaces. In an embodiment, liquid is nebulised from the transducer surface. In another embodiment, liquid is nebulised from the non-transducer surface. In another embodiment, liquid is nebulised from both the transducer and opposing non-transducer surfaces.

The piezoelectric substrate and electroacoustic transducer according to the present invention is preferably also used to sense a liquid mass on the at least one substrate. Unlike in U.S. Pat. No. 6,679,436 (Omron) where a surface wave, i.e., the SAW, is used for the sensing, a bulk wave, i.e., a BAW generated on the same substrate is used for the sensing in the present invention.

The electroacoustic transducer for the nebuliser according to the present invention may be an interdigital transducer (IDT), and the at least one piezoelectric substrate may be formed of Lithium Niobate ($LiNbO_3$).

In an embodiment, at least a portion of the non-transducer surface may further include a coating comprising at least one metal. In an embodiment, at least a portion of the transducer surface at the distal end of the substrate may further include a coating comprising at least one metal. The at least one metal may be titanium, gold, aluminium, chromium or combinations thereof.

The piezoelectric substrate may have a thickness at or around a wavelength of the SAW propagated in the transducer surface. This optimises the generation of SRBWs within the substrate.

In the nebuliser according to the present invention, the liquid may be nebulised to form droplets having a size across a range between 0.1 μm to 100 μm. Furthermore, the liquid may be nebulised at a nebulisation rate up to 10.0 ml/min.

The mount may include a shelf upon which the substrate is mounted, the shelf including one or more gaps for preventing liquid creep along the substrate.

According to a preferred embodiment of the nebuliser according to the present invention, the housing may be in the form of a cartridge having an external electrical contact connected to the at least one electroacoustic transducer, and an integral liquid supply system.

According to another aspect of the present invention, there is provided a method of nebulising a liquid using a nebuliser as described above.

The method may include nebulising liquid to form liquid droplets having a size of across a range between 0.1 μm to 100 μm. The smaller droplet sizes between 1 and 5 μm are ideal for applications for the inhalation of therapeutic agents. It is however to be appreciated that liquid droplets of a larger size beyond 10 μm could be formed if required for other applications including fragrances, cosmetics, pesticides, paints or antiseptics.

The method may further include nebulising liquid at a nebulisation rate up to 10.0 ml/min.

The method may preferably include nebulising liquid including functional or therapeutic agents therein such as pharmaceuticals, plasmid DNA, RNAi-derived products, peptides, proteins and cells, or, non-therapeutic agents such as perfume, cosmetics, antiseptics, pesticides or paints.

The use of both the transducer and non-transducer surfaces for fluid delivery and nebulisation in the nebuliser according to the present invention not only provides a much higher nebulisation rate (1 ml/min and greater, compared to typical 0.1-0.2 ml/min SAW nebulisation rates) but also circumvents undesirable heating due to viscous dissipation of the acoustic wave energy when it is coupled to the materials typically used for fluid delivery in the previous nebulisation configurations (glass, wick, PDMS, etc.), which typically have poor acoustic matching properties. In addition, the preferred configuration of the nebuliser according to the present invention also preferably reduces the contact of chemicals and sensitive samples with the electroacoustic transducer. This has advantages of protecting the electrodes of the transducer from harsh chemicals as well as protecting any sensitive biological samples from the intense electric field generated by the electrodes.

BRIEF DESCRIPTION OF THE INVENTION

It will be convenient to further describe the invention with reference to the accompanying drawings which illustrate preferred embodiments of the nebuliser according to the present invention. Other embodiments are possible, and consequently, the particularity of the accompanying drawings is not to be understood as superseding the generality of the preceding description of the invention.

Figure 5A:
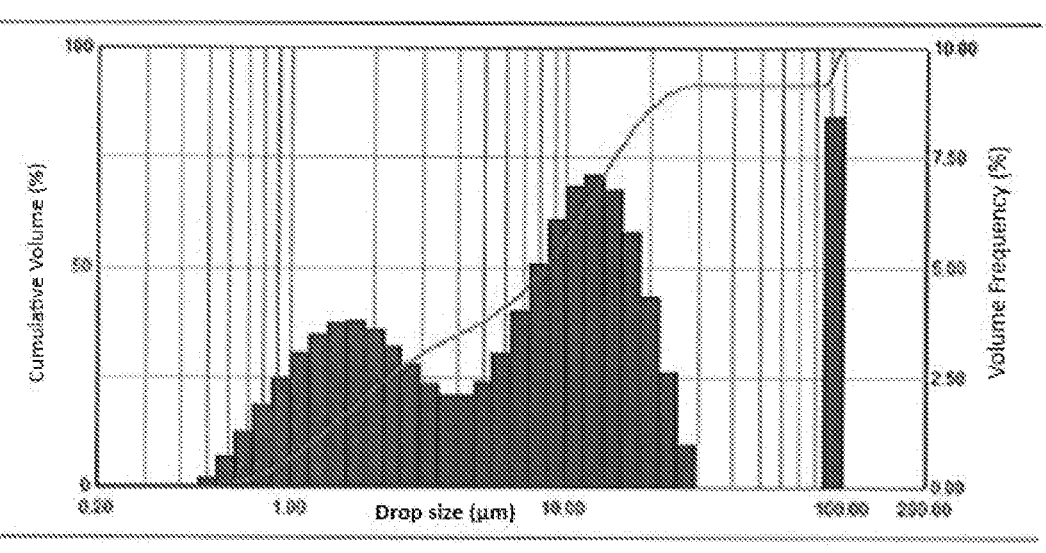
Figure 5B:
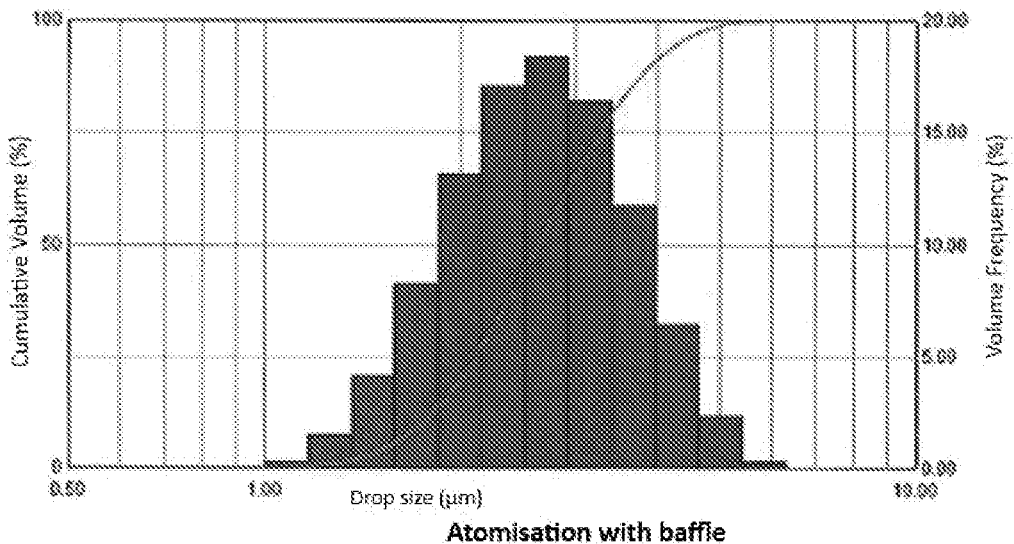
Figure 6:
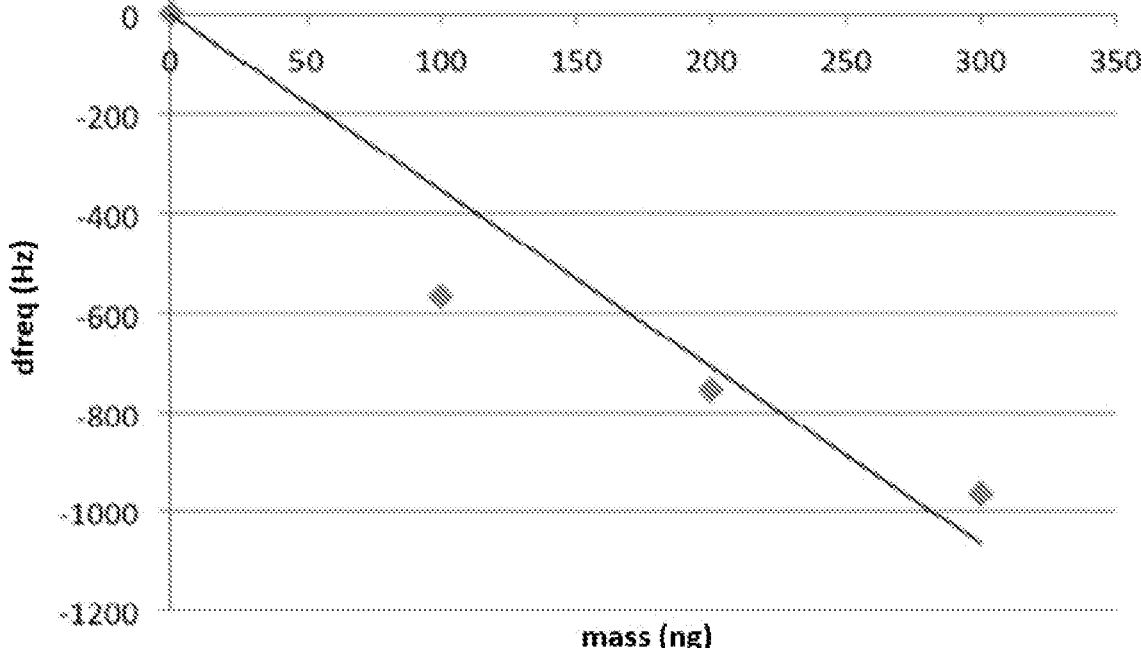
Figure 7:
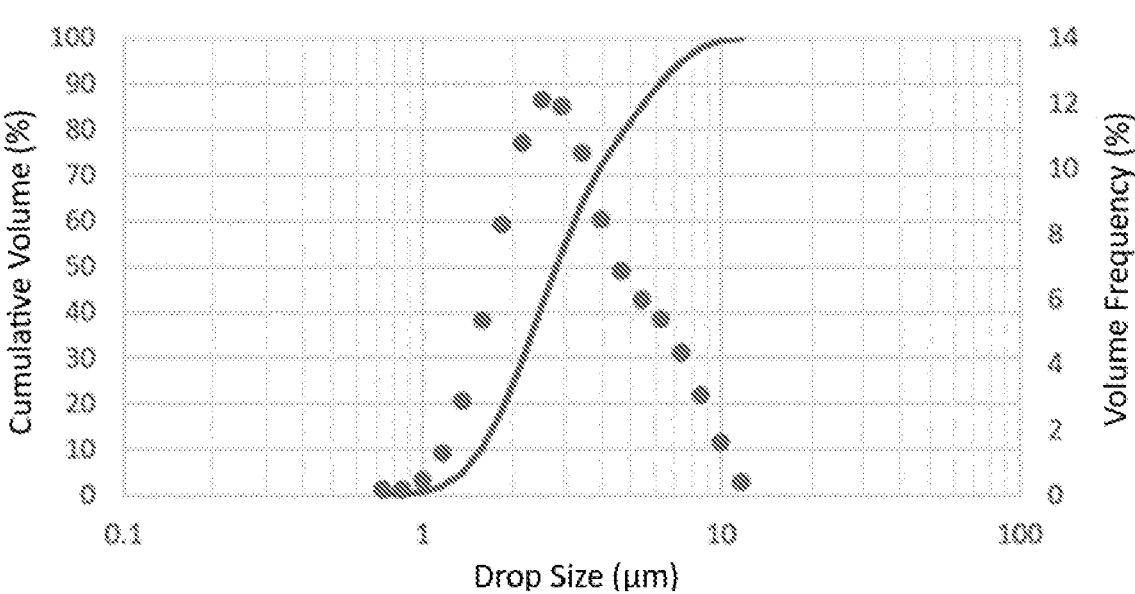

FIG. 5*a* is a graph of the ejected drop size distribution for a nebuliser according to the present invention without a baffle;

FIG. 5*b* is a graph of the ejected drop size distribution for a nebuliser according to the present invention with a baffle;

FIG. 6 is a graph showing the mass sensing of Humalog (insulin medication) as a function of frequency; and FIG. 7 is a graph showing atomisation distribution data of a nebuliser according to one embodiment of the present invention wherein the non-transducer substrate surface is coated with titanium and gold.

DETAILED DESCRIPTION OF THE INVENTION

Figures 1A, 1B, 1C, 1D, 1E:
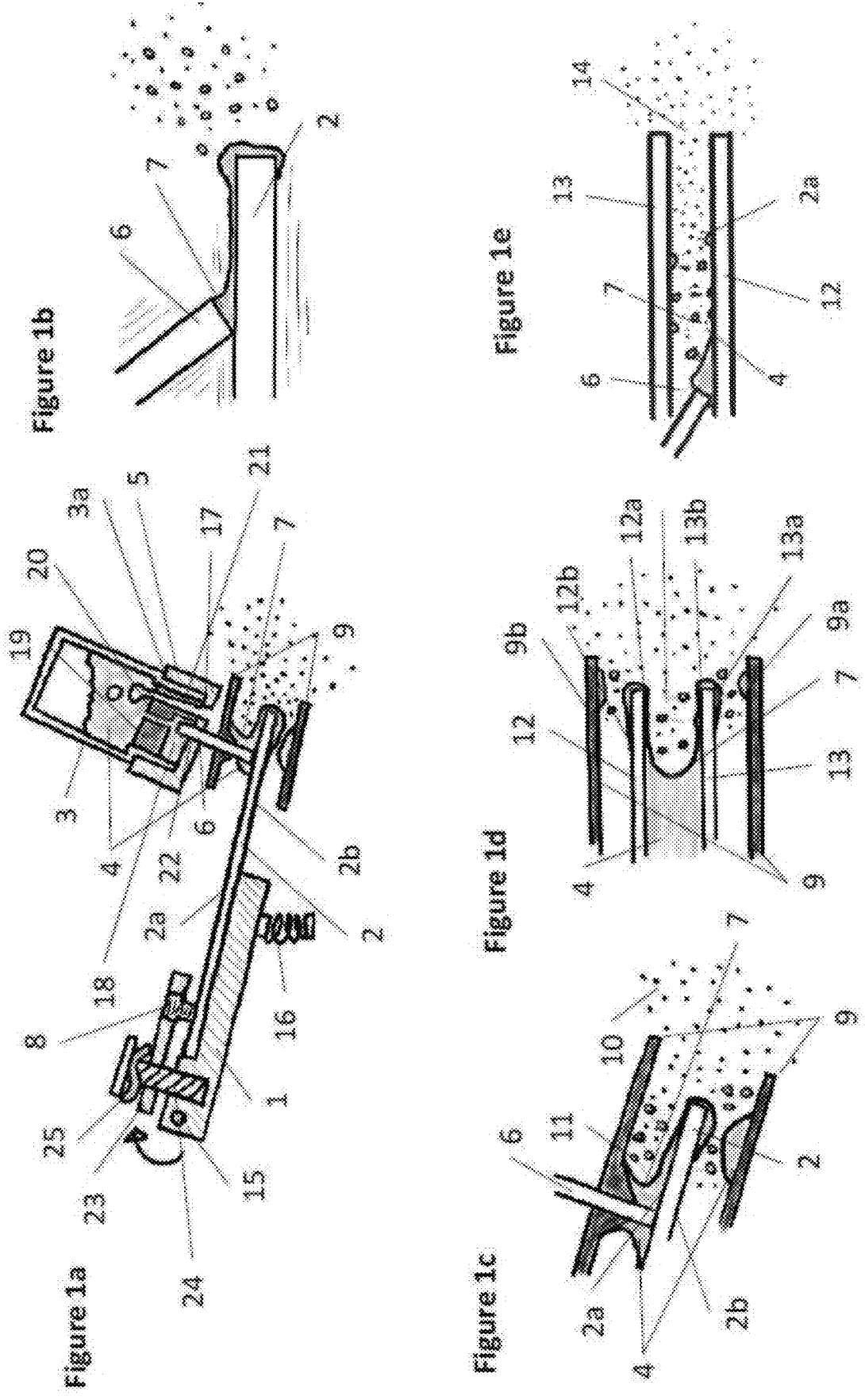
FIG. 1a is a side cross-sectional view of a nebuliser according to one embodiment of the present invention.
FIG. 1b is a magnified view of the liquid delivery system which, according to one embodiment, constitutes a nib or needle.
FIG. 1c is a side detailed view of a nebuliser according to one embodiment of the present invention.
FIG. 1d is a detailed side cross-sectional view of another embodiment of a nebuliser according to the present invention.
FIG. 1e is a side cross-sectional view of another embodiment of a nebuliser according to the present invention.

Referring initially to FIGS. 1*a* and 1*c*, there is shown a first preferred embodiment of a nebuliser according to the present invention. The nebuliser includes a mount 1 which supports the piezoelectric substrate 2. The piezoelectric substrate 2 includes a transducer surface 2*a* upon which is located an electroacoustic transducer in the form of an interdigital transducer (IDT) (not shown). The substrate 2 further includes a non-transducer surface 2*b* located in a parallel adjacent relationship relative to the transducer surface 2*a*.

The nebuliser further includes a liquid reservoir 3 within which is accommodated the liquid 4 that is to be nebulised by the nebuliser. The reservoir 3 can be in the form of a bottle or vial having a threaded neck 3*a* that can be screwed into a threaded inlet opening 5 provided on a housing (not shown). The nebuliser is shown in its in use position in FIGS. 1*a* and 1*c* which thereby allows the liquid 4 to be gravity fed from the reservoir 3 and through a relatively rigid supply conduit in the form of a nib or needle 6. A liquid meniscus 7 is formed at the end of the nib or needle 6 on the transducer surface 2*a* (FIG. 1*b*). RF power is supplied to the IDT via electrical contacts 8. This will result in surface acoustic waves (SAWs) being generated in the transducer surface 2*a* which in turn generates surface reflected bulk waves (SRBWs) that are reflected between the transducer and non-transducer surfaces 2*a*, 2*b*. The unique hybrid wave configuration of the SRBWs combined with SAWs allows for liquid 4 to be drawn from the liquid meniscus 7 across the transducer surface 2*a*. If liquid 4 build-up occurs at the end of the transducer surface 2*a* the acoustic wave energy will pull the liquid 4 around the substrate 2 end and onto the non-transducer surface 2*b* of the substrate 2 where the liquid 4 can also be nebulised. The gravity fed arrangement allows for continuous, self-regulated flow of the liquid to prime the needle or nib 6.

To elaborate further, the supply pump, gravity feed or capillary action in the nib or needle 6 in the present invention simply acts to prime it. The liquid 4 is then pulled out by the acoustic wave onto the surfaces of the substrate 2, as illustrated in FIG. 1*b*. It is therefore preferable that the liquid delivery system, i.e., the nib or needle 6, is in contact with the substrate 2. This is in contrast to the capillary-driven liquid delivery to supply channels etched into the substrate in International Publication No. WO2012/096378 (Panasonic Corp.). Having the acoustic wave drawing out the liquid from the nib or needle 6 onto the substrate 2 avoids flooding since only as much liquid that is nebulised is drawn out onto the device.

The choice of material for the nib or needle 6 should preferably comprise an acoustically reflecting material. Acoustically-absorbing materials tend to absorb and hence dampen the acoustic energy on the substrate 2. Such materials may include metals, polymer or ceramic materials.

The housing furthermore includes at least one baffle 9, which can, for example, be formed by the wall of the housing, spaced from the transducer surface 2*a* and positioned in a generally parallel and adjacent relationship to the transducer surface 2*a*. Earlier nebuliser designs have used meshes to try to control and maintain uniformity in the size of the nebulised droplets. However, such meshes are prone to clogging. The baffle 9 however provides a simpler means of asserting control over the uniformity of the droplet sizes. Larger droplets 11 having a size in the 10 μm to 100 μm order are ejected off the substrate surface 2*a* with greater momentum than smaller droplets. Due to the angle (known as the Rayleigh angle) at which the acoustic wave energy couples into the liquid 4. This gives rise to the droplets being ejected as they are nebulised at the same angle. These larger droplets 11 then impact on the surface of the baffle 9 so that they are redirected back to the substrate surface 2*a* where they are re-fed into the existing liquid feed from the reservoir 3. The liquid that formerly was part of the returned droplets 11 are therefore subjected again to nebulisation. Smaller droplets 10 having a size in the order of around 1 μm, on the other hand, have significantly less momentum and hence do not reach the surface of the baffle 9. Rather, the small droplets 10 are entrained into the airflow out of the nebuliser. A similar droplet size control process also occurs between the non-transducer surface 2*b* and the corresponding baffle surface 9 adjacent to the non-transducer surface 2*b*.

FIG. 1*d* shows another embodiment of the nebuliser according to the present invention utilising at least two piezoelectric substrates 12, 13 supported in a stacked configuration within the nebuliser. More than two piezoelectric substrates can also be stacked in parallel and adjacent locations within the nebuliser. Each piezoelectric substrate 12, 13 will have a similar arrangement to the embodiment shown in FIGS. 1*a* and 1*c* with an electroacoustic transducer located on a transducer surface 12*a*, 13*a* of each substrate 12, 13 to allow for acoustic wave energy to be generated within each substrate to thereby draw nebulised liquid supplied to both the substrate surface 12*a*, 13*a* and parallel adjacent non-substrate surface 12*b*, 13*b* of each substrate 12, 13. The housing also includes a lower baffle 9*a* that is located parallel and adjacent to the transducer surface 13*a* of the lower substrate 13 which assists in droplet size control as previously described. A similar effect occurs between the non-transducer surface 12*b* of the upper substrate 12 and the baffle 9*b* opposite to that surface. The orientation of the transducer 12*a*, 13*a* and non-transducer 12*b*, 13*b* surfaces of the two substrates 12, 13 is not important in this embodiment and they may be interchanged as long as the surfaces are parallel and adjacent to one another. This arrangement however provides a further means for controlling the uniformity of the droplet size. Liquid is also trapped between the interstitial space 14 between the two substrates 12, 13, and between the transducer surface 13*a* of the lower substrate 13 and the lower baffle surface 9*a*, and between the non-transducer surface 12*b* of the upper substrate 12 and the upper baffle surface 9*b*. The thickness of the liquid meniscus 7 is a critical parameter in controlling the droplet size. Therefore, adjustment of the relative spacing between each substrate 12, 13 and baffle surfaces 9*a*, 9*b* allows the meniscus thickness to be controlled, thereby providing uniformity in the nebulised droplet size. This configuration therefore allows for the droplet size to be controlled by adjusting the above noted spacing. It is also envisaged that multiple droplet sizes could be obtained by having multiple spacings FIG. 1e shows another embodiment of the nebuliser according to the present invention utilising at least two piezoelectric substrates 12, 13 supported in a stacked configuration within the nebuliser. Like the embodiment described in FIG. 1d, liquid is trapped between the interstitial space 14 between the two substrates 12, 13. Unlike in FIG. 1d, the liquid meniscus 7 need not be in contact with both substrates 12 and 13. Furthermore, the nib or needle 6 may, in an embodiment, be in direct contact with the surface of one of the substrates 12 to deliver the liquid 6. In another embodiment, the nib or needle 6 may not be in contact with the surface of the substrate 12, but may be positioned such that the liquid 6 is delivered to be in contact with the surface of the substrate 12. It is envisaged that the at least two piezoelectric substrates 12, 13 may be the same or may be different. For example, one or more of the substrates may be patterned as described in detail below to provide further control of the nebulizer output parameters.

Furthermore, in view of the arrangements in FIGS. 1d and 1e, for example, a higher nebulisation rate can be provided because there are now multiple substrate surfaces from which nebulisation can occur. An adjacent substrate surface can also act as an active baffle where spurious large droplets ejected from one substrate surface are collected onto the surface of an adjacent substrate and re-nebulised until smaller droplets are produced. This approach may be considered active substrate baffling rather than a passive physical baffle provided by a housing inner wall. This system may be enhanced by promoting standing waves or regions of standing waves using the aforementioned techniques.

The same piezoelectric substrate 2, 12, 13 and IDT can also be triggered at a lower frequency corresponding to the fundamental thickness mode (BAW) of the substrate (around 3.5 MHz for a 500 μm thick substrate) to employ a sensing functionality. The rationale for using the thickness mode for sensing is because single crystals such as, but not limited to the 128 YX lithium niobate piezoelectric crystal used, naturally have a high-quality factor Q on the order of between $10^4$ to $10^6$. Therefore, such a platform can simultaneously perform both efficient nebulisation as well as efficient mass sensing with a limit of detection down to 10 ng. Both functions can be achieved with the same electrode patterns unlike other known devices that incorporate different electrode patterns for different microfluidic functions. Therefore, the nebuliser according to the present invention can add the functionality of sensing mass residual during nebulisation in order to determine, by subtraction from the total dose delivered, the actual dose that is administered to the user.

In the above embodiment in FIGS. 1a and 1c, the liquid 4 is gravity fed to a nib or needle 6. The nib or needle 6 presses onto the end of the transducer surface 2a, bringing liquid 4 into contact with the transducer surface 2a where it can be atomised into droplets 10, 11. Robust contact between the nib or needle 6 is achieved by displacing the mount 1 towards the nib or needle 6 which is pre-loaded with a force and exerts a constant pressure under displacement (not shown). In one embodiment, the pre-loaded force is achieved by fixing the mount 1 to a cantilever, or by configuring the mount 1 with a pivot 15 and a resilient member in the form of a spring 16 arrangement that are fixed to the housing (not shown), for example. The displacement of the mount 1 caused by the pressing of the nib or needle 6 onto the substrate 2 allows constant pressure and contact between the end of the nib or needle 6 and the transducer surface 2a to be realised, and for a meniscus 7 to form and be sustained. This meniscus 7 provides pressure equal to that of the sealed reservoir 3 so that liquid does not flow freely from the reservoir 3 onto the substrate. The capacity for the mount 1 to be displaced and exert pressure means that a rigid nib or needle 6 can be used in direct contact with the substrate effectively. Referring to FIG. 1b, the nib or needle resonates with the acoustic wave energy, allowing the acoustic wave energy to draw liquid 4 from the nib or needle 6 across the substrate surface 2. During nebulisation of the liquid 4, the loss of liquid 4 will diminish the meniscus 7. The negative pressure that arises then draws further liquid 4 through the nib or needle 6 to replenish the meniscus 7. When the relative pressure of the reservoir 3 is sufficiently low due to the outflow of liquid 4 through the nib or needle 6, an air bubble will enter the reservoir 3 via the inlet hole 17 to balance the pressure and allow liquid 4 to be drawn by the nib or needle 6. This process will continue until the reservoir 3 is exhausted. It is envisaged that multiple nibs or needles could be used to increase flow rate and increase the reliability of the system. It is, however, also envisaged that a pressure release valve be used to provide a controlled flow of liquid onto the transducer surface 2a. It is further envisaged that the end of the substrate 2 be submerged in a meniscus, where the liquid is provided by a closely situated orifice. Alternatively, it is envisaged that an active pumping system, such as a syringe or peristaltic pump be used to actively feed liquid onto the substrate surface 2a. An active pumping system may be preferred in situations where liquid having a high surface tension and/or high viscosity needs to be delivered to the transducer surface 2a.

A flow regulator 19 may also be used in conjunction with the above described gravity feed system, adjacent orifice, or active pumping system. It is also envisaged that a flow regulator 19 works in a similar fashion to a fountain pen. Such an arrangement is shown in FIG. 1a where fluid within a reservoir 3 flows into an inner chamber 18 via a flow regulator 19. The flow regulator 19 includes a liquid outlet passage 20 through which liquid 4 can pass, and an air inlet passage 21 connected to the reservoir 3. The flow regulator 19 therefore provides a steady feed of liquid 4 that would otherwise be disrupted by the release of air bubbles that enter through the inlet passage 21 to thereby balance the air pressure externally and within that reservoir 3. The liquid 4 is delivered to an inner chamber 18. The inner chamber 18 connects to the nib or needle 6, and has a peripheral opening 22 within which is accommodated the nib or needle 6. The nib or needle 6 is therefore constantly wetted by the liquid 4.

The electrical contact end of the substrate 2 is pressed and in direct contact with the mount 1 in order to dissipate localised heating that can damage the substrate 2. This pressing can be achieved by applying pressure through contact cantilevers 23 with broad electrical contacts 8 embedded in them, for example—broad electrical contacts 8 also mitigate damaging arcing between the electrical contacts 8 and the substrate 2 under the high voltages that occur during nebulisation. Pressure to the contact cantilever 23 bases can be applied via magnetic attraction effects, or by using a screw 24 to push down spring washers 25, for example. Alternatively, pressure may be applied through spring loaded electrical contacts. Furthermore, it is envisaged that a conductive material may be directly bonding to the IDTs as an alternative to electrical contacts. A heat sinking surface (not shown), which could be integrated into the mount 1, can also be utilised by the pressing of the nib or needle 6 onto the parallel substrate 2, which can then remain in contact with the heat sink and cool the substrate 2 during nebulisation. This heat sink may also feature geometry that retains a small amount of excess liquid in contact with the nebulisation end of the substrate 2 to further increase the robustness of the system while nebulisation is occurring. The mount 1 may also be made of a conductive material such as metal, which will allow the ready discharge of excess pyroelectrically induced charge. This reduces the chance of damaging arcing across the substrate 2, increasing the life of the substrate 2.

Figure 2:
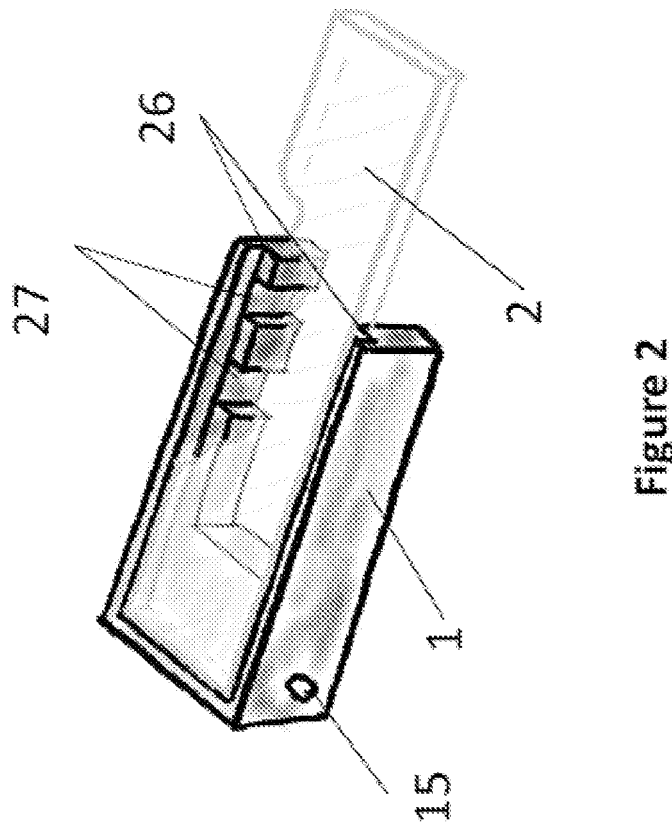
FIG. 2 is a perspective of a platform that holds a piezoelectric substrate for the nebuliser according to the present invention.

Referring now to FIG. 2, the mount 1 holds the substrate 2 along its side edges on a narrow shelf 26 so that if any wetting occurs between the mount 1 and the substrate 2 the acoustic wave energy will not be damped as it travels along the substrate 2. There are also provided gaps 27 along the narrow shelf 26 of the mount 1, which prevent liquid 4 from creeping up the substrate 2 between the contact of the substrate 2 and the mount 1.

Figure 3:
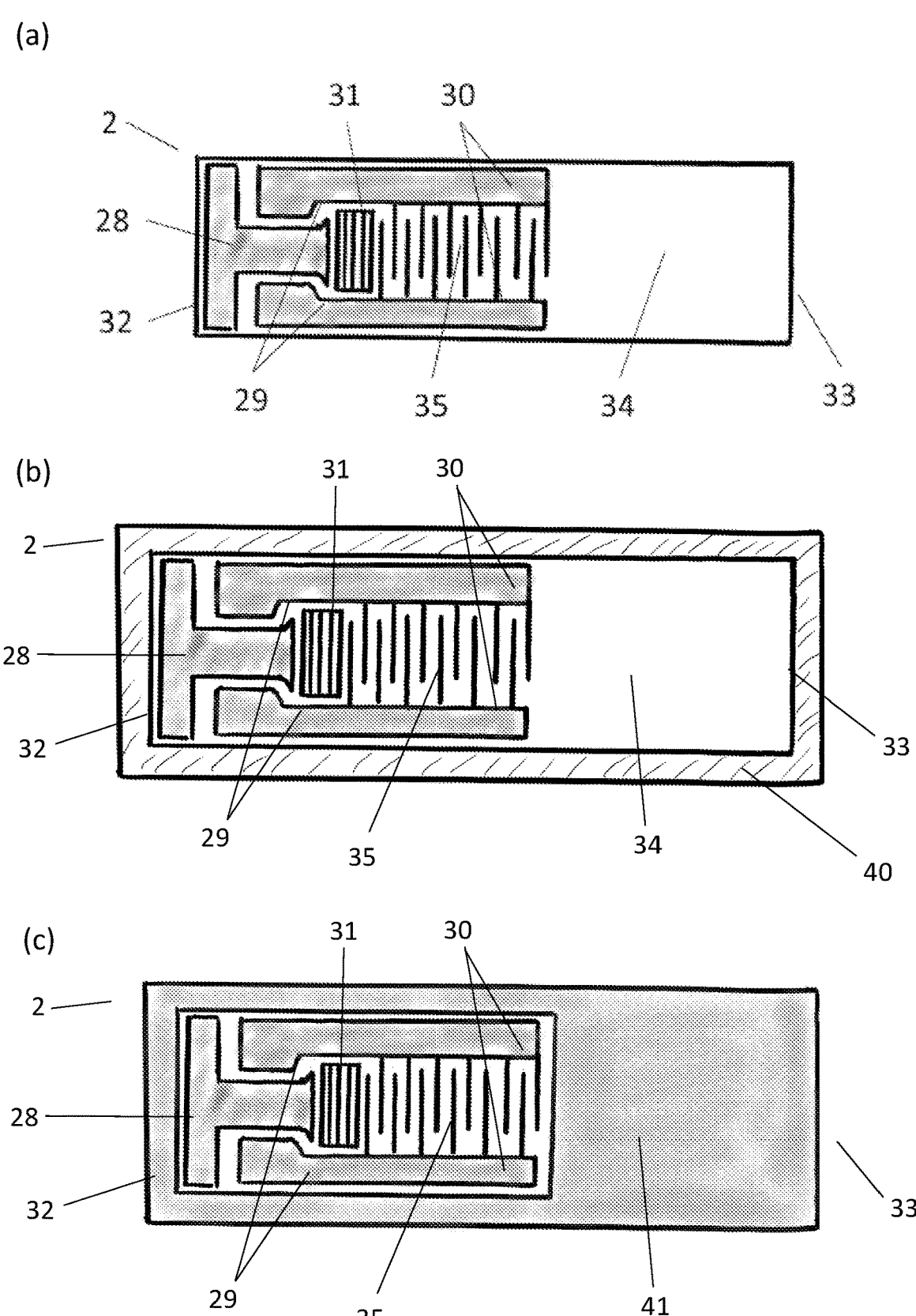
FIG. 3a is an orthogonal view of a transducer surface of a nebuliser according to the present invention.
FIG. 3b is an orthogonal view of a transducer surface of another embodiment of the described nebuliser highlighting the perimeter surface of the substrate. As described, compliant absorbent material may be in contact with at least a portion of the perimeter surface of the substrate surfacer highlighted in FIG. 3b.
FIG. 3c is an orthogonal view of a transducer surface of another embodiment of the described nebuliser highlighting coating on the distal end of the transducer surface and areas suitable for patterning.
FIG. 3d is a representative example of the described nebuliser wherein the non-transducer surface of the described nebuliser is partially coated.
FIG. 3e is an orthogonal view of a transducer surface of another embodiment of the described nebuliser highlighting coating on the distal end of the transducer surface of the substrate.
Figure 3:
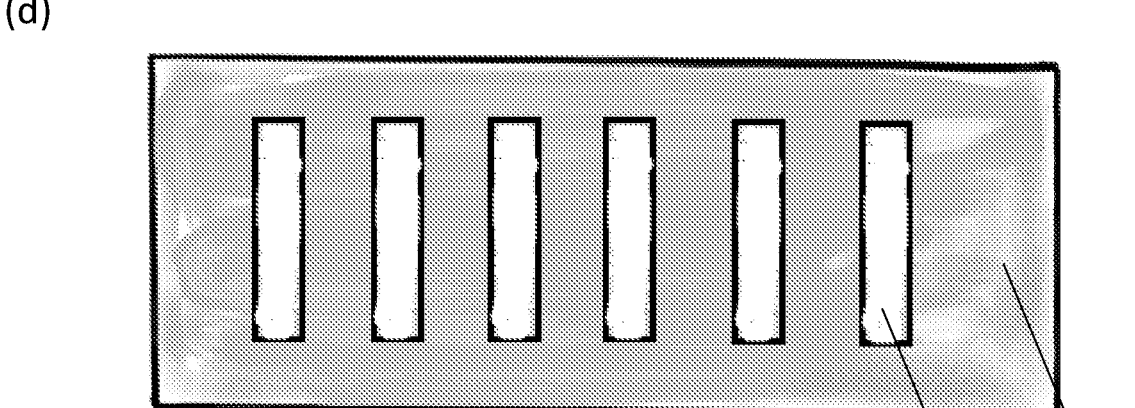
Figure 3:
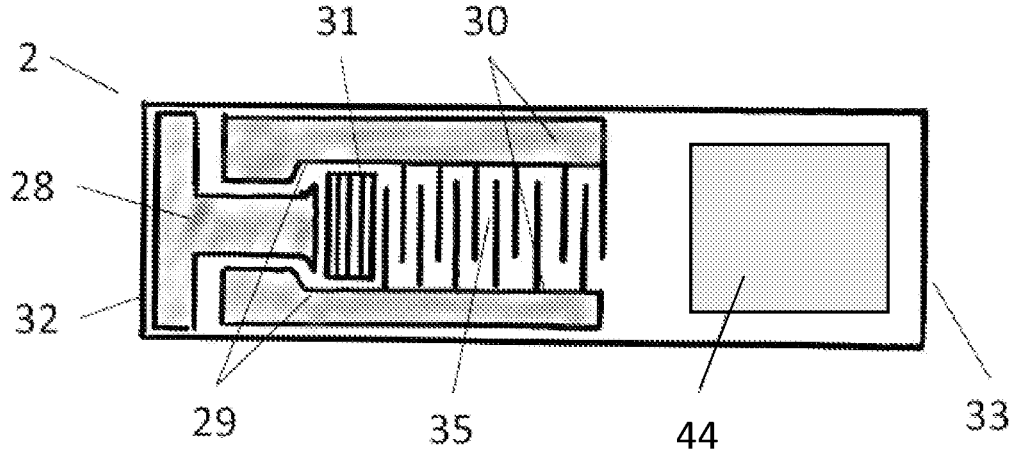

Referring now to FIG. 3(a), the transducer surface 2a possesses surface features, such as a shield 28, bends 29 in the main IDT bars 30, and reflector bars 31 at the electrical contact end 32 that disrupt the progression of acoustic wave energy and encourage reflection and absorption of potentially damaging acoustic wave energy at the electrical contact end 32. Reflected acoustic wave energy aids in the nebulisation of liquid at the nebulisation end 33 of the substrate 2. Bare surface 34 lies between the end of the main IDT bars 30 and the nebulisation end 33 of the device to mitigate contact between the nebulising liquid and the IDTs 35.

In another embodiment, the described nebuliser may further comprise a compliant absorbent material in contact with at least a portion of the perimeter surface of the substrate. For example, the perimeter surface of the substrate is highlighted as a hashed region 40 in FIG. 3(b). It is appreciated that the compliant absorbent material may be in contact with at least a portion of the perimeter surface 40 highlighted in FIG. 3(b). It has surprisingly been found that the durability of the chip may be enhanced by the addition of a compliant material in contact with at least a portion of the perimeter surface of the substrate. Without wishing to be bound by theory, it is considered that the addition of a compliant material may disperse or reduce excess vibrations in and/or on the chip. Furthermore, it is considered that the addition of a compliant material may prevent overheating or localized superheating in and/or on the substrate. This reduces the rate of substrate failure, providing increased reliability and use from the nebulizer without damage or failure. For example, suitable compliant materials, may include pastes, tapes, or compliant solids. In an embodiment, the compliant material is adhesive tape. In an embodiment, the compliant material is silicone rubber. In an embodiment, the compliant material is thermal paste. In an embodiment, the compliant material comprises a portion of the housing in contact with the perimeter of the chip.

In an embodiment, the compliant absorbent material may be in contact with at least a portion of the perimeter of the distal end of the substrate. In an embodiment, the compliant absorbent material may be in contact with at least a portion of one or more sides of the surface of the perimeter of the substrate. In an embodiment, the compliant absorbent material may be in contact with a portion of one or more sides and a portion of the distal end of the substrate. In particular, placement around at least a portion of the perimeter surface allows acoustic radiation in the atomisation region of the substrate to be sufficient to achieve atomisation.

It has further been found that coating at least a portion of the non-transducer side of the substrate may alter wave reflections and the standing wave ratio (SWR). In one embodiment, the coating may comprise one or more metals. In an embodiment, the coating is formed from titanium, gold, aluminium, chromium and combinations thereof. The inventors have surprisingly found coating at least a portion of the non-transducer surface of the substrate with one or more metals may reduce overheating. Additionally, the inventors have surprisingly found that coating at least a portion of the non-transducer surface of the substrate provides a degree of control and/or the ability to tune the standing wave and traveling wave components in SAW, SRBW and combinations thereof. It has surprisingly been found that solid coatings or partial coatings effect the travelling and standing wave components present on and in the substrate. A representative example is shown in FIG. 3(d), that is, the non-transducer surface 43 of the substrate being partially coated 42. The standing wave ratio may be further modified by adjusting parameters such as coating hardness, thickness, and/or roughness. It has been observed that adjusting the standing wave ratio between 1 and infinity can increase the stability and atomisation rates of the substrate. By way of example, atomisation distribution data is represented in FIG. 7, wherein non-transducer substrate surface was coated with titanium and gold. As a result of the coating, the overall droplet distribution was tighter as measured by geometric standard deviation (GSD). By comparison, when an uncoated chip is used, two separate peaks in droplet distribution of nebulized fluids are typically observed. It is considered that this results from promotion or preference of travelling wave components rather than standing wave components in this system. Conversely, where the chip is coated, promotion or preference for standing wave components rather than traveling wave components is observed. By modifying the ratio of travelling and standing wave components, parameters including the droplet size and geometric standard deviation may be controlled or adjusted. These parameters are further described below. In one or more embodiments, the described nebuliser may utilise traveling wave components, standing wave components and/or combinations thereof. In one or more further embodiments, the described nebuliser may utilise standing wave components in SAW, standing wave components in SRBW, traveling wave components in SAW, traveling waves components in SRBW, permutations and combinations thereof.

In addition to coatings applied to the non-transducer surface, the inventors have surprisingly found coating at least a portion of the transducer surface of the substrate with one or more metals may reduce overheating. In particular, the inventors have found that where at least a portion of the transducer surface further includes a coating at the distal end of the substrate, chip failure due to overheating or pyroelectric failure is reduced or eliminated providing a more efficient and robust system. In one embodiment, the coating on the transducer surface may comprise one or more metals. In an embodiment, the coating is formed from biocompatible metals, including titanium, gold, and combinations thereof. Representative examples are shown in FIGS. 3(c) and 3(e), that is, wherein the entirety of the transducer surface of the substrate includes a coating 41 (FIG. 3c) and wherein at least a portion of the transducer surface of the substrate includes a coating 44 at the distal end of the substrate (FIG. 3e).

In another embodiment, the described nebuliser may further comprise patterning of conductive material on a portion of the substrate surface. As used herein, the terms "patterning" and "patterned" and variations thereof, refers to techniques such as photolithography, which transfer a geometric pattern on to a given substrate. Such techniques are typically used for patterning in the chip industry. Generally, a coating, especially a metal coating as described, is applied and the surface subsequently patterned by lithography or other means. In an embodiment the transducer substrate surface is patterned. In another embodiment, the non-transducer substrate surface is patterned. It has surprisingly been found that the addition of patterning (in areas other than functional areas of the transducer surface of the substrate) may aid in dissipating or reducing localised superheating and/or pyroelectrically induced charge. It is further understood that the non-transducer surface of the substrate may alternatively or additionally may be patterned. FIG. 3(c) highlights the functional areas of the transducer surface of the substrate (including the main IDT bars 30, the IDTs 35, shield 28, bends 29, reflector bars 31). One of the areas of the transducer surface of the substrate suitable for patterning includes the coated surface 41 highlighted in FIG. 3(c) in grey. A skilled person would understand that such patterning may be placed in any region of the surface of the chip which still enables the device to function as a nebulizer.

In addition, it has been found that adjustments in the standing wave ratio may also be achieved by positioning multiple sets of IDTs such that the resultant waves interact. By way of example, it is envisaged that patterning of IDTs may disrupt destructive acoustic waves and reduce unwanted overheating for example, which in turn increases the reliability of the resultant chip. Furthermore, in an embodiment, the substrate may be patterned or coated in such a way to provide discrete regions wherein either standing or traveling waves are promoted. It is envisaged that such an arrangement provides further tunability in a range of output parameters of the nebulized liquids.

While embodiments utilising a needle or a nib have been described, still other embodiments are envisaged wherein the at least one supply conduit may include a wick or a microchannel. The choice of a specific supply conduit may be dependent, in part, on how the conduit operates in combination with other features of the nebuliser system.

Figures 4A, 4B:
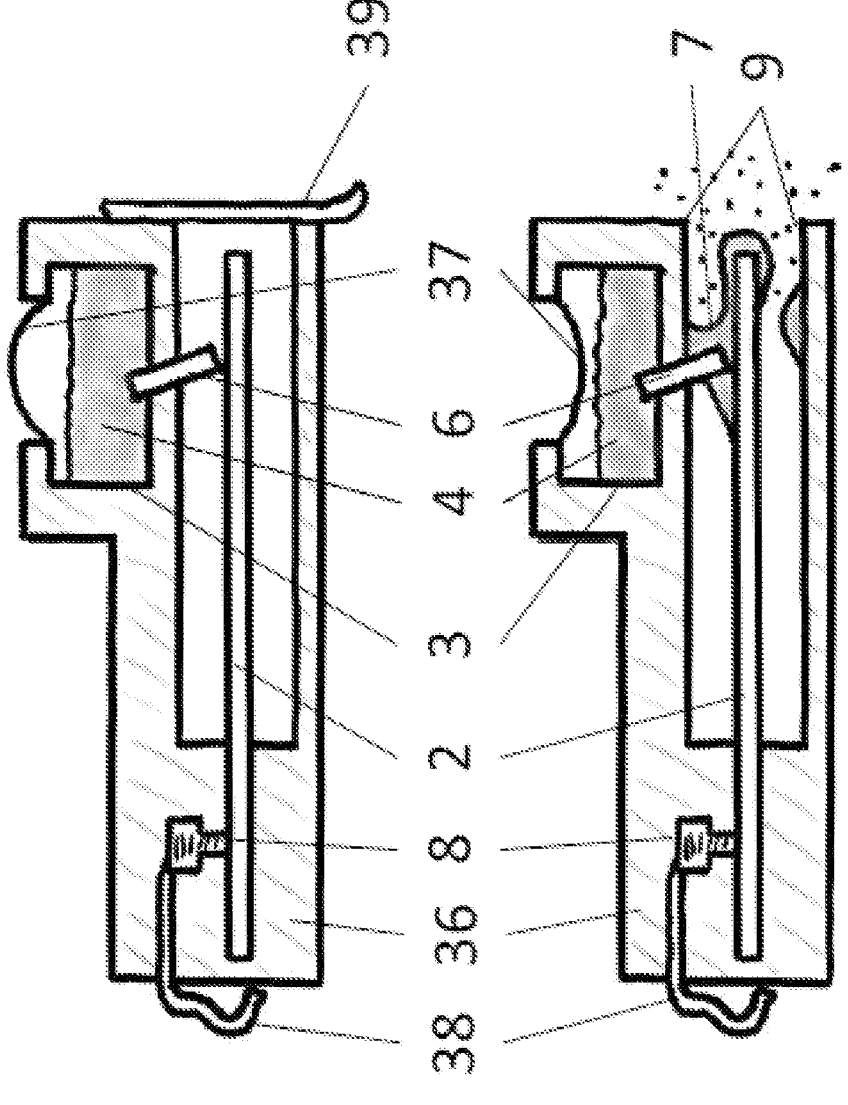
FIGS. 4a and 4b are side cross-sectional views of another embodiment of a nebuliser according to the present invention.

FIGS. 4a and 4b depict another preferred embodiment of the nebuliser according to the present invention. This arrangement integrates the substrate 2 and other key components into a single integrated housing or cartridge 36 which can be interfaced with an external housing that features the appropriate electrical system and flow chamber of a nebuliser (not shown), and used as a single or multiple dose cartridge 36 that can be disposed of after use. The reservoir 3 can be formed from a cavity in the cartridge 36, where one surface of it can be a deformable blister or button 37 that can be depressed; this can displace liquid inside the reservoir and serve to prime the liquid 4 in the needle or nib 6, or deposit a full dose of liquid 4 onto the substrate 2 to form a meniscus 7—other means of displacing the liquid 4 such as a syringe plunger are also possible. FIG. 4a represents the system before the blister 37 is depressed and the liquid 4 deposited, and FIG. 4b shows the system after the blister 37 has been depressed, causing liquid 4 deposition. RF power can be supplied to the substrate via exposed spring contacts 38 that are connected to the broad electrical contacts 8 that are in contact with the substrate 2. The exposed spring contacts 38 allow the cartridge 36 to be interfaced with an external body that can house the appropriate nebuliser electrical systems and flow chamber (not shown). The surrounding parallel surfaces around the substrate 2 act as baffle surfaces 9 to control drop size and recirculate excess liquid 4. The cartridge can be protected by a seal 39 that can be breached or removed before liquid 4 is nebulised or when the cartridge 36 is interfaced with the external body of the nebuliser. This cartridge can incorporate any combination of the features described and shown in FIGS. 1a, 1c, 1d, 1e, 2 and 3a, 3b, 3c or 3d.

The presented circuit is a miniaturised handheld circuit running at high frequency (10 MHz). The main reason for overcoming the miniaturisation bottleneck, where alternative Radio Frequency (RF) circuits are bulky, is due to the simplicity of the circuit. Unlike common RF circuits where most critical components commonly and intuitively rely on digital data and programming to track the target frequency and trigger various ad-on components such as sensor driver, powering buttons, etc., this circuit utilises a robust, stable, fixed, single frequency regardless the loading nature on the circuit. In addition, the circuit is capable of sensing user breathing patterns to drive the nebuliser and/or run by a triggering button, it maintains only an analogue data transfer and actuation for the entire circuit.

The circuit, although small and compact, provides dual triggering methods by either, 1—continuously pressing or toggling a button or 2—'smart' triggering via user inhalation, where the triggering time is predetermined, thus accommodating a user inhaling for too long. Therefore, this allows for a precise administration time and therefore known dosage.

The above-mentioned counter-intuitive circuit design approach, utilising analogue data transfer working in RF domain, has allowed the circuit to be driven via a small 11.1V (3 cell) Lithium-polymer battery.

FIG. 5a shows the ejected drop size distribution without the use of a baffle 9. The graph shows that a large proportion of the droplets have a size in the 10 µm to 100 µm range. FIG. 5b shows the ejected drop size distribution when a baffle 9 is used. That graph shows that large droplets in the 10 µm to 100 µm size are minimised.

For sensing, the optically flat single crystal substrate allows for bulk (eg. Lamb) wave resonances that have large quality factors Q in the order of $10^4$ to $10^6$. Therefore, very small mass loadings on the surface of the substrate can produce detectable frequency shifts so as to allow mass sensing of samples down to 10 ng sensitivity. This is shown in the graph of FIG. 6 which shows the mass sensing of Humalog (insulin medication). The graph shows a linear frequency shift with increasing mass, with the sensitivity of 100 ng.

SAW nebulisers have found application in a variety of fields, including in the administration of active agents. Inhaled medication is the most common form of therapy for asthma, chronic obstructive pulmonary disease (COPD) and for other respiratory conditions, such as obstructive bronchitis, emphysema, and cystic fibrosis. For example, corticosteroids, bronchodilators and β2 agonists are typically administered by inhalation for treatment of asthma, COPD and other respiratory conditions. It is envisaged that the described nebulizer may be used in conjunction with a range of possible active agents. Suitable active agents include, but are not limited to, corticosteroids (such as Fluticasone, Budesonide, Mometasone, Beclomethasone, and Ciclesonide), bronchodilators (such as Salmeterol or Albuterol, Formoterol, Vilanterol, Levalbuterol and Ipratropium). By way of example, Albuterol, also referred to as salbutamol or Ventolin, is a β2 agonist and short-term bronchodilator that opens up the medium and large airways in the lungs. Ipratropium, also referred to as Ipratropium bromide, is a muscarinic antagonist (a type of anticholinergic) which opens up the medium and large airways in the lungs. Budesonide, also referred to as BUD, is a type of corticosteroid used for the long-term management of asthma and chronic obstructive pulmonary disease (COPD). In an embodiment, the described nebulizer is adapted for delivery of Albuterol. In an embodiment, the described nebulizer is adapted for delivery of Ipratropium. In an embodiment, the described nebulizer is adapted for delivery of Budesonide.

The described nebulizer advantageously provides reliable, efficient and accurate delivery of active agents. The resultant nebulised liquids may be characterized by one or more parameters. It is appreciated that each active agent has differing physicochemical properties. Furthermore, it is appreciated that various parameters of the described nebuliser may be optimised for delivery of a given active agent, including droplet size (microns), geometric standard deviation (GSD), volumetric atomization rate, stabilization period (i.e. time to use), fraction of API administered, trajectory losses, and fine particle fraction.

In an aspect, the described nebuliser provides control of the droplet size of nebulised liquids. In particular, the droplet size of nebulised liquids may be optimised for a given active agent. In an embodiment, the described nebuliser provides nebulised liquids wherein the droplet size is in the range of from 0.1 and 100 μm, preferably in the range of from 0.1 to 10 μm, preferably in the range of from 0.5 to 7.5 μm, more preferably in the range of from 1 to 5 μm, even more preferably in the range of from 2 to 4 μm. In an embodiment, the described nebuliser provides nebulised liquids wherein the droplet size is <10 μm, preferably <8 μm, preferably <6 μm, preferably <5 μm, preferably <3 μm.

In an aspect, the described nebuliser provides control of geometric standard deviation (GSD) of the droplets of nebulised liquids. In particular, the GSD of nebulised liquids may be optimised for a given active agent. In an embodiment, the described nebuliser provides nebulised liquids wherein the GSD is <10 μm, preferably <8 μm, preferably <6 μm, preferably <5 μm, preferably <3 μm, preferably <2.5 μm, preferably <2.1 μm.

In an aspect, the described nebuliser provides control of the stabilization period (i.e. time to use). Advantageously, the described nebuliser provides reduced stabilization periods (i.e. time to use). Short or reduced stabilization periods provide reduced lagtime to use, increased efficiency, reduction in sample loss or fluid loss, and improved accuracy with dosing and administration of active agents. In particular, the stabilization period may be optimised for a given active agent. In an embodiment, the described nebuliser provides a stabilization period of <1 sec, preferably <0.5 sec, preferably <0.25 sec, preferably <0.1 sec, preferably <0.05 sec, preferably <0.03 sec, preferably <0.02 sec, preferably <0.01 sec.

In an aspect, the described nebuliser provides control of the volumetric atomization rate of nebulised liquids. In particular, the volumetric atomization rate of nebulised liquids may be optimised for a given active agent. In an embodiment, the described nebuliser provides nebulised liquids wherein the volumetric atomization rate is in the range of from 0.1 to 10 mL/min, preferably in the range of from 0.15 to 7.5 mL/min, preferably in the range of from 0.2 to 5 mL/min. In an embodiment, the described nebuliser provides nebulised liquids wherein the volumetric atomization rate is >0.1 mL/min, preferably >0.25 mL/min, preferably >0.3 mL/min, preferably >0.35 mL/min, preferably >0.4 mL/min, preferably >0.45 mL/min, preferably >0.5 mL/min, preferably >0.55 mL/min, preferably >0.6 mL/min, preferably >0.65 mL/min, preferably >0.7 mL/min, preferably >0.75 mL/min.

In an aspect, the described nebuliser provides control of the fraction of API administered in nebulised liquids. In particular, the fraction of API administered may depend on the physicochemical properties of a given active, but may be optimised for a given active agent with the described system. In an embodiment, the described nebuliser provides nebulised liquids wherein the fraction of API administered is >60%, preferably >65%, preferably >70%, preferably >75%, preferably >80%, preferably >85%, preferably >90%, preferably >95%, preferably >97%, preferably >98%, preferably >99%.

In an aspect, the described nebuliser provides control of the trajectory losses in nebulised liquids. In particular, the trajectory losses may be optimised for a given active agent. In an embodiment, the described nebuliser provides nebulised liquids wherein the trajectory loss is <20%, preferably <15%, preferably <10%, preferably <9%, preferably <8%, preferably <7%, preferably <6%, preferably <5%.

In an aspect, the described nebuliser provides control of the fine particle fraction of nebulised liquids. Fine particle fraction is generally understood as a measure of mass depositing in the lung during inhalation of nearly isotonic nebulized aerosols. The amount of aerosol inhaled in different fine particle definitions is compared to the amount of aerosol depositing in the lung and alveolar regions for nearly isotonic nebulized aerosols. It is accepted that droplet stages 1-7 have 65% drug in a form that accumulates or targets deep lung tissue. The fine particle fraction may depend on the physicochemical properties of a given active, but may be optimised for a given active agent with the described system. In an embodiment, the described nebuliser provides a fine particle fraction of >20% in droplet stages 1-7, preferably >30%, preferably >35%, preferably >40%, preferably >45%, preferably >50%, preferably >55%, preferably >60%, preferably >65%, preferably >70%, preferably >75%.

In addition to the active agents described, the described nebuliser may be adapted to nebulise fluids or samples comprising delicate molecules and particles (e.g. DNA, RNAi-derived products, peptides, proteins and cells) without denaturing them while maintaining high nebulisation throughout (typically above 1 ml per minute). Prior art nebulisers are to date limited to between 0.1 to 0.4 ml/min thereby necessitating long inhalation times, typically from tens of minutes to an hour. This has therefore limited the practical uptake of conventional nebulisers. The higher nebulisation rates that can be achieved by the nebuliser of the present invention can significantly shorten the administration time.

Nebulisers in accordance with the invention have been subject to human clinical trials to determine efficiency of delivery of active agents to the lungs by inhalation using Technetium-99m DTPA aerosol ([$^{99m}$Tc]DTPA aerosol). Initial results indicate the described nebulizer systems provide effective delivery of nebulized active agent to the target tissue.

TABLE 1

| Unadjusted clinical results from initial human clinical trials with [$^{99m}$Tc]DTPA aerosol | | | | |
|---|---|---|---|---|
| | Volunteer 1 | Volunteer 2 | Volunteer 3 | Volunteer 4 |
| Right lung dose (MBq) | 8.25 | 27.1 | 21.9 | 26.6 |
| Left lung dose (MBq) | 7.15 | 25.2 | 22.2 | 23.3 |
| Total lung dose(MBq) | 15.4 | 52.3 | 44.1 | 49.9 |

Modifications and variations as would be deemed obvious to the person skilled in the art are included within the ambit of the present invention as claimed in the appended claims.

The invention claimed is:

1. A nebuliser for nebulising liquid droplets, including:
a housing;
a piezoelectric substrate accommodated within the housing, the piezoelectric substrate having:
a transducer surface upon which is located at least one electroacoustic transducer for generating acoustic wave energy within the piezoelectric substrate, and
an opposing non-transducer surface; and
a liquid supply system for supplying a liquid to at least one of the group consisting of the transducer surface and the non-transducer surface, the liquid supply system including a reservoir for accommodating the liquid, and at least one supply conduit for supplying the liquid from the reservoir to the piezoelectric substrate, the at least one supply conduit arranged to be in contact with the liquid on the piezoelectric substrate during supply,
wherein the liquid supply system is configured to prime the supply of liquid such that the supply of liquid to the piezoelectric substrate is regulated by acoustic wave energy generated within the piezoelectric substrate pulling liquid from the liquid supply system and does not comprise a wick in contact with the piezoelectric substrate.

2. The nebuliser according to claim 1, wherein the at least one supply conduit is formed from an acoustically reflecting material.

3. The nebuliser according to claim 1, wherein the liquid is gravity fed from the reservoir through the at least one supply conduit.

4. The nebuliser according to claim 1, wherein the liquid is transferred from the reservoir through an active pumping system.

5. The nebuliser according to claim 1, wherein the liquid supply system further includes a flow regulator for providing a steady flow of liquid therefrom, further wherein the flow regulator includes a liquid outlet passage through which the liquid can pass, and an air inlet passage connected to the reservoir.

6. The nebuliser according to claim 1, further including a control means for controlling the size of the nebulised liquid droplets.

7. The nebuliser according to claim 6, wherein the control means includes at least one baffle located in a generally parallel and adjacent relationship to at least one of the transducer surface and the non-transducer surface.

8. The nebuliser according to claim 7, wherein the baffle is provided by a housing inner wall located in a parallel adjacent relationship from at least one of the transducer surface and the non-transducer surface.

9. The nebuliser according to claim 1, wherein the housing accommodates two of the piezoelectric substrates of claim 1, such that there are two piezoelectric substrates accommodated by the housing including the piezoelectric substrate of claim 1, the two piezoelectric substrates being spaced apart and located in a parallel adjacent relationship to define a spacing between the two piezoelectric substrates.

10. The nebuliser according to claim 9, wherein the nebuliser provides a droplet size control means, the droplet size control means including pre-setting the spacing between the two piezoelectric substrates to control the thickness of the meniscus of the liquid supplied between the two piezoelectric substrates, to thereby control the size of the nebulised droplets.

11. The nebuliser according to claim 9, wherein the nebuliser provides a droplet size control means and the housing includes internal walls, and the droplet size control means includes pre-setting the spacing of the two piezoelectric substrates from the internal walls of the housing to control the thickness of the meniscus of the liquid supplied between the two piezoelectric substrates and the internal walls, to thereby control the size of the nebulised droplets.

12. The nebuliser according to claim 1, wherein the piezoelectric substrate and the electroacoustic transducer is used to sense the liquid on the piezoelectric substrate.

13. The nebuliser according to claim 1, wherein the piezoelectric substrate includes a perimeter surface, and the nebuliser further including:
a compliant material in contact with at least a portion of the perimeter surface.

14. The nebuliser according to claim 13, wherein the compliant material is selected from the group consisting of adhesive tape, silicone rubber and thermal paste, or combinations thereof.

15. The nebuliser according to claim 1, wherein the acoustic wave energy includes surface acoustic waves (SAW) propagated in the transducer surface of the piezoelectric substrate.

16. The nebuliser according to claim 1, wherein the acoustic wave energy includes surface reflected bulk waves (SRBW) reflected between the transducer surface and the non-transducer surface of the piezoelectric substrate.

17. The nebuliser according to claim 1, wherein the acoustic wave energy includes a combination of surface acoustic waves (SAW) propagated in the transducer surface of the piezoelectric substrate and surface reflected bulk waves (SRBW) reflected between the transducer surface and the non-transducer surface of the piezoelectric substrate.

18. The nebuliser according to claim 1, wherein at least a portion of the non-transducer surface further includes a coating comprising at least one metal.

19. The nebuliser according to claim 1, wherein the piezoelectric substrate includes a distal end, and at least a portion of the transducer surface further includes a coating at the distal end of the piezoelectric substrate comprising at least one metal.

20. The nebuliser according to claim 1, wherein the liquid is nebulised from the transducer surface, the non-transducer surface, or both the transducer surface and the non-transducer surface.

21. A method of nebulising a liquid using a nebuliser according to claim 1.

22. The method of nebulising the liquid according to claim 21, wherein the liquid includes functional or therapeutic agents, or, non-therapeutic agents, or combinations thereof.

23. The nebuliser according to claim 1, wherein the at least one supply conduit is in contact with the substrate.

24. The nebuliser according to claim 23, wherein the at least one supply conduit is in the form of a nib or needle.

25. The nebuliser according to claim 1, wherein the at least one supply conduit is in the form of a nib or needle.

* * * * *